United States Patent [19]

Daniell, Jr.

[11] 4,320,747

[45] Mar. 23, 1982

[54] SLIDABLY-COUPLED JOINT

[76] Inventor: Roy B. Daniell, Jr., 4221 N. Shallowford Rd., Apt. 4, Chamblee, Ga. 30341

[21] Appl. No.: 194,469

[22] Filed: Oct. 6, 1980

[51] Int. Cl.$^3$ .............................................. A61F 3/00
[52] U.S. Cl. ....................................... 128/80 C; 3/22
[58] Field of Search ...................... 128/80 C, 87 R, 88; 3/22; 403/52, 112, 113

[56] References Cited

U.S. PATENT DOCUMENTS

| 3,779,654 | 12/1973 | Horne | 3/22 X |
| 3,817,244 | 6/1974 | Taylor | 128/80 C |
| 3,958,569 | 5/1976 | Vosburgh | 128/80 C |

Primary Examiner—John D. Yasko
Attorney, Agent, or Firm—Vivian L. Leon; Harry I. Leon

[57] ABSTRACT

An artificial joint for a knee or elbow brace in which the axis around which motion takes place is not fixed but rather follows the natural joint. An eccentric member extends from one of the joint elements into a guide formed in the other joint element and is threadedly engaged with a retaining screw to hold the joint elements in overlapping relation. Simultaneously, an elongated pin protrudes from the inner face of the joint element having the guide into a tapered groove formed in the joint element from which the eccentric member extends. The depth of the groove is less than the thickness of the joint element in which it is formed within the zone of overlap. The abutments of the eccentric member against the edge surfaces of the guide and of the pin against the edge surfaces of the groove, either simultaneously or at different times, limit the relative movements of the joint elements and provide support for a wearer's joint. At full extension, the eccentric member and the pin each abut an edge surface to lock the joint so as to prevent any increase in the angle between the longitudinal axes of the joint elements. For the treatment of an injured joint, one or more inserts may be placed in the groove to reduce the travel of the pin. For athletic use, the artificial joint is incorporated in a knee brace having improved straps to provide freedom of movement of both the natural joint and the large muscles of the leg. Because both the guide and the groove are totally enclosed, the joint can be used in severe environments such as the playing fields of contact sports.

11 Claims, 10 Drawing Figures

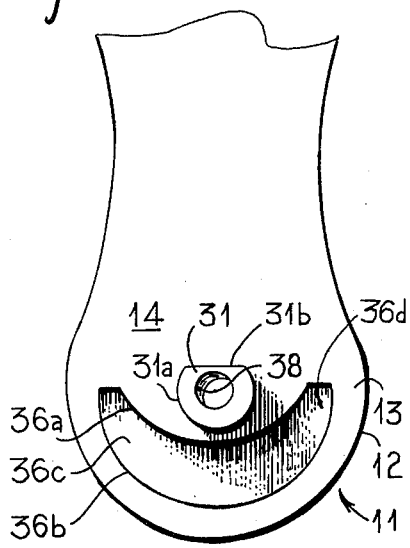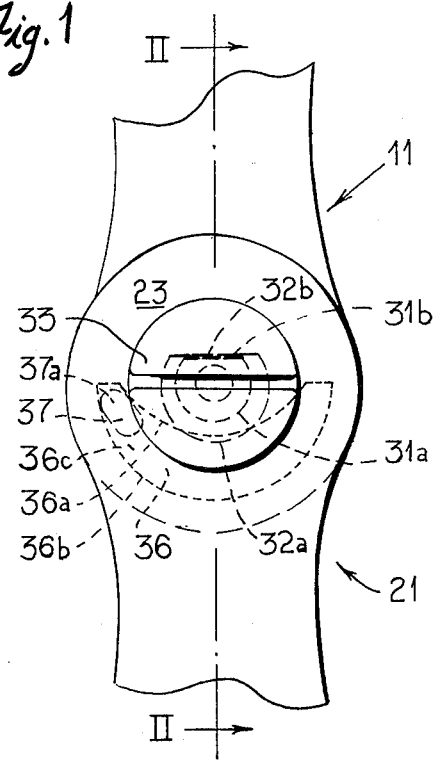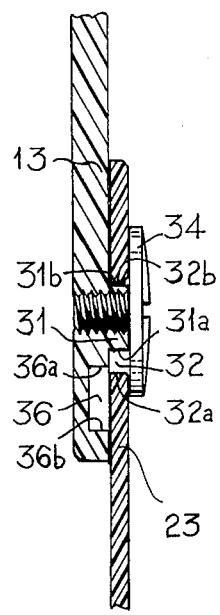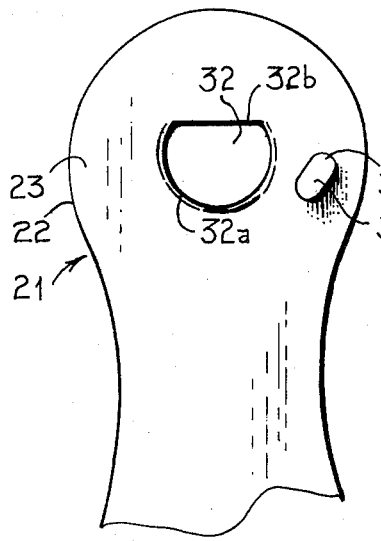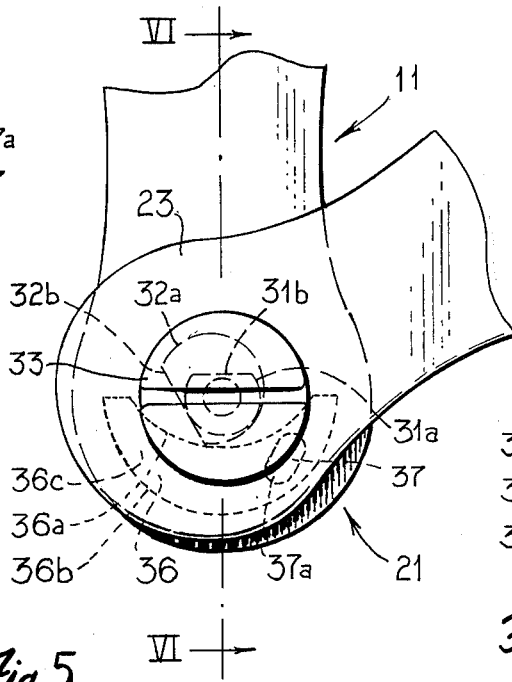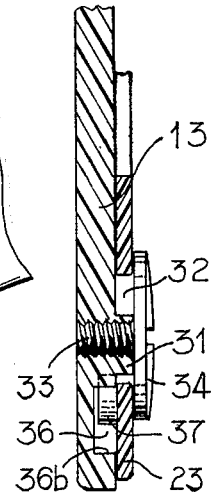

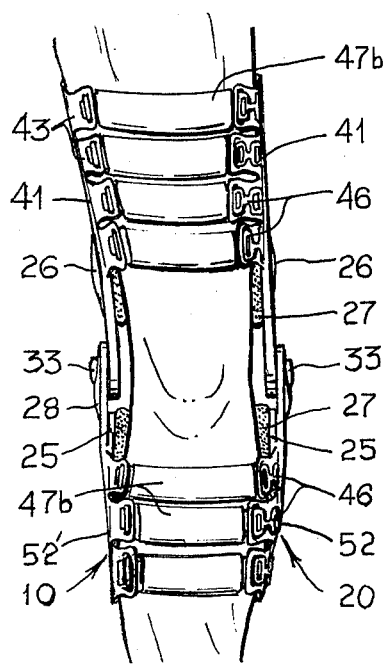
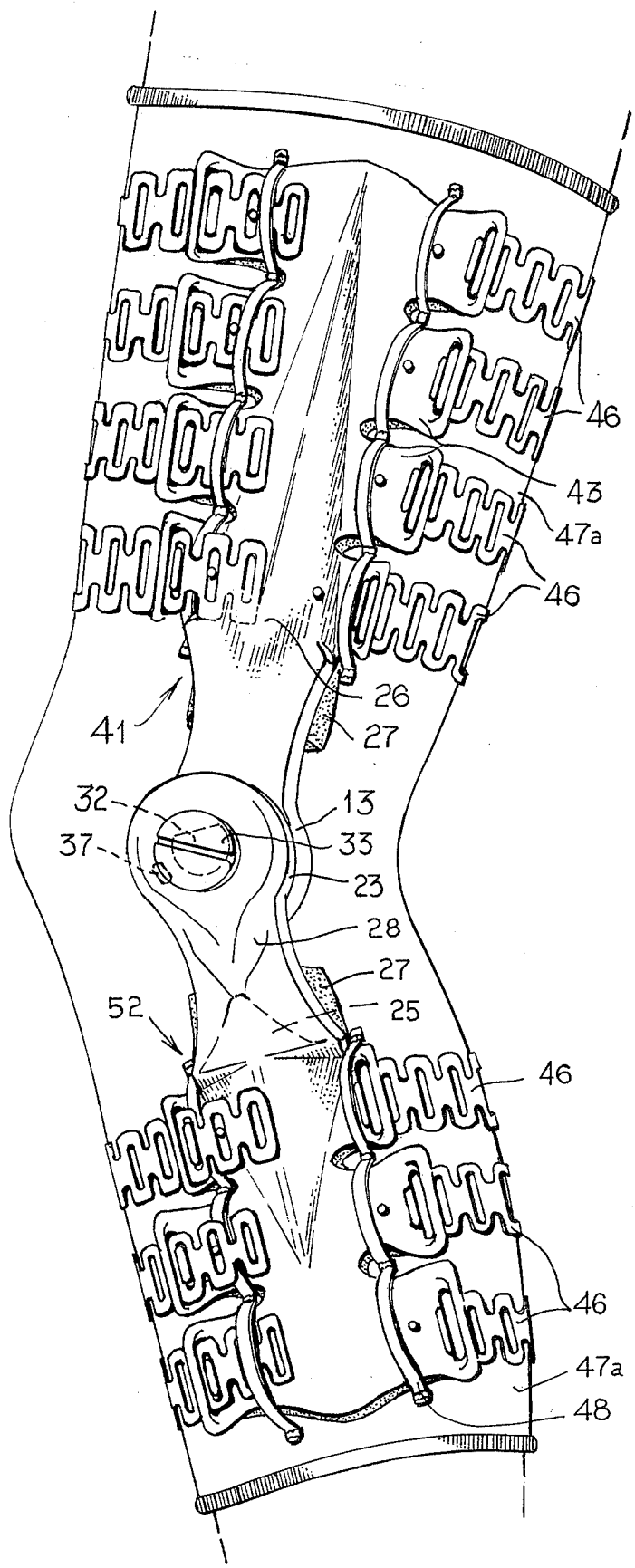

SLIDABLY-COUPLED JOINT

BACKGROUND OF THE INVENTION

1. Field of the Invention

The present invention relates generally to a joint for a brace for the natural slide and hinge joints in the human body. More particularly, it relates to such a joint which is slidably-coupled and which has a means for limiting the relative angular movements of the pivotally interconnected joint elements. It has specific application in contact sports in which braces are worn by athletes in order to reduce the chance of injury to the knee area and the extent of injury thereto from both forward and lateral blows and from adverse twisting. It may also be used as a load-supportive and motion-controlling joint in the rehabilitation of a damaged or diseased joint at the knee and elbow.

2. Description of the Prior Art

Slidably-coupled joints having both single and dual pivots for use in knee braces and the like have been described in the prior art. The advantages of the slidably-coupled joints are well recognized: they allow natural movement in a healthy joint and have less tendency to migrate up and down a wearer's limb and cause abrasion of the wearer's skin.

Artificial joints for knee and elbow braces having a means for limiting the relative angular movements of slidably-coupled joint elements have already been described in U.S. Pat. No. 3,779,654. In the cited patent, the joint has dual pivots which abut against edge surfaces formed in the joint elements to prevent hyperextension of the wearer's joint. The dual pivots do not move independently of each other, however. The pivot pins move in narrow slots, the widths of which are only slightly greater than the diameters of the sleeves in which the pivot pins are journalled; the position of one pivot pin determines the position of the other pivot pin. As a result, the articular motion is constrained to follow a definite path. The slots must be contoured individually to fit each wearer to avoid binding of the wearer's joint. Only a single side member in a brace incorporating such an artificial joint is practicable. Since two connected side members are required in a brace to protect a wearer's joint from torsional twisting, this artificial joint is ill-suited for use in knee braces worn by athletes participating in football, basketball, rodeo, or similar sports. Moreover, the narrow slots are exposed to allow both pivot pins to interconnect the joint elements for added strength over that afforded by a single pivot pin; such slots are highly vulnerable to jamming by clothing and other foreign objects. Consequently, the slots are undesirable for use in the applications disclosed in the cited patent which included their incorporation in artificial limbs as well as in braces designed for athletic and for orthopedic purposes.

Slidably-coupled joints of the prior art having a single pivot pin, on the other hand, allow the articular motion to be made of any combination of rotation and translation and thus can be used in a knee brace or the like having two connected side members. However, each slidably-coupled, single pivot pin joints have no means for confining the joint elements to move with respect to each other on one side of the position in which they are in longitudinal alignment. Therefore, they are incapable of preventing hyperextension of the wearer's joint. As a further consequence, these joints are not suitable for use in orthopedic devices in which a limited freedom in the relative movements of the joint elements is desirable in order to promote rapid healing and reduce joint stiffness and the atrophy of a patient's muscles. Moreover, such joints tend to be weak with the single connecting pivot pin frequently failing under the stress of longitudinal loads such as those incurred in the knee braces of athletes participating in contact sports.

Furthermore, none of the slidably-coupled joints of the prior art have been incorporated in a knee brace or the like designed to be worn by athletes which both allows freedom of motion of the large muscles of a wearer's limb as well as of the natural joint itself. In such a brace, the comfort derived from the capability of the slidably-coupled joint to follow the natural movement of the wearer's joint is at least partially annulled by the discomfort experience by the wearer, during running, due to the binding and chafing caused by the straps.

SUMMARY OF THE INVENTION

The present invention comprises a slidably-coupled joint structure which might be incorporated in a lateral brace or in an apparatus having connected lateral and medial braces. The joint structure comprises a pair of joint elements with overlapping end portions. A guide having a straight edge surface is formed in the end portion of the first joint element. Protruding into the guide from the contiguous face of the second joint element is an eccentric member with a shoulder. The eccentric member and a retaining screw which is threadedly engaged therewith comprise a means for retaining the end portions of the joint elements in overlapping relation. The shoulder abuts against the straight edge surface of the guide when the joint elements are aligned in a limiting position to one side of which the joint elements are movable with respect to one another.

In the same face of the second joint element from which the eccentric member protrudes, a tapered groove is formed. The groove has curved edge surfaces which have radii of curvature of different lengths; the width of the groove decreases in a direction toward at least one of its distal portions. An elongated pin connected to the first joint element moves within the groove; as the angle between the longitudinal axis of the joint elements is increased, the elongated pin migrates into the portion of the groove having decreased width. Near the end of the groove, the elongated pin abuts one of the curved edge surfaces; as the angle between the longitudinal axes of the joint elements is further increased, the first joint element pivots about the elongated pin, thus bringing the shoulder into positive contact with the guide to lock the joint with respect to further extension.

The guide further includes a curved edge surface connecting the ends of the straight edge surface. Prior to the abutment of the elongated pin against one of the curved edge surfaces of the groove, the eccentric member is in sliding contact with the curved edge surface of the guide whenever a load parallel to one of the longitudinal axes of the joint elements is imposed upon the joint, thereby providing ample support of a wearer's joint during flexion.

The tapered groove is made inaccessible from the outside by having the depth of the groove be less than the thickness of the end portion of the second joint element in which it is formed. To eliminate the possibility that the joint can be jammed inadvertently with foreign objects, the retaining screw is provided with a head which is of sufficient diameter to cover the guide for all of the relative positions into which the joint elements can move.

An insert which may be placed within the tapered groove prior to the assembly of the joint comprises a means for adjusting the limiting position to one side of which the joint elements are movable with respect to one another so that a wearer's limb can be only partially extended. A pair of inserts to be placed within the tapered groove on either side of the elongated pin are also provided so that the joint can be immobilized when required for the treatment of an injured or diseased joint. As the joint heals, the amount of relative motion allowable between the joint elements can be gradually increased by substituting shorter inserts. Thus a patient can exercise the muscles of the limb with the injured or diseased joint and reduce the atrophy and joint stiffness which would otherwise develop if the joint were immobilized throughout the duration of the healing process.

It is accordingly a major object of this invention to provide a joint for a brace which is capable of substantially following the actual motion of the knee and elbow in which the relative angular motion of the joint elements is limited, the joint elements being movable with respect to one another to one side of a position wherein the joint elements are in longitudinal alignment.

It is a further object of this invention to provide a joint for a brace which inhibits hyperextension of the knee without exposing the wearer to injury from the means for limiting the angular motion of the joint elements or from foreign objects jamming the limiting means.

It is a still further object of this invention to provide a slidably-coupled joint for a brace in which the relative angular motion of the joint elements is limited, the joint elements being movable with respect to one another to one side of a position wherein the angle between the longitudinal axes of the joint elements is less than 180°, this limiting position being adjustable by means of inserts which are detachably mounted within the joint.

It is a still further object of this invention to incorporate a slidably-coupled joint and improved straps in a knee brace or the like to provide an apparatus designed to be worn by athletes participating in contact sports which provides adequate protection of the wearer's joint from lateral blows and from adverse twisting and, at the same time, allows freedom of movement of both the wearer's joint and the large muscles of the wearer's limb.

These and further objects will be evident from the following disclosure, taken along with the accompanying drawings, which illustrate the preferred embodiments of the joint.

BRIEF DESCRIPTION OF THE DRAWINGS

FIG. 1 is a frontal elevational view of a joint structure according to the present invention for a lateral brace designed for use on the left knee or on the right elbow and for a medial brace designed for use on the right knee or on the left elbow.

FIG. 2 is a cross-section II—II from FIG. 1;

FIG. 3 is a frontal elevational view of the inner face of the upwardly extending joint element shown in the assembled joint structure according to FIG. 1;

FIG. 4 is an elevational view of the inner face of the downwardly extending joint element shown in the assembled joint structure according to FIG. 1;

FIG. 5 is a frontal elevational view of the joint structure according to FIG. 1 in which the joint elements are moved to a configuration which they may obtain during the flexion of a wearer's knee joint;

FIG. 6 is a cross-section VI—VI from FIG. 5;

FIG. 7 is a perspective view of a side member of a knee brace incorporating the joint structure according to FIG. 1 in which the side member is secured to a wearer's leg with improved straps;

FIG. 8 is a frontal elevational view on a reduced scale of a knee brace having a medial side member according to FIG. 7 and a lateral side member;

Like reference characters indicate corresponding parts throughout the several views of the drawings.

DESCRIPTION OF THE PREFERRED EMBODIMENTS

The present joint structure is designed to follow closely the natural movement of the articulated body joints of the human body. The articulated joints with which this disclosure is concerned are specifically the knee and the elbow.

The varieties of movement which it is possible to perform at any given joint of the human body depend on two factors: the shape of the articulating surfaces and the presence of restraining ligaments. Movement at the elbow joint is limited by the shape of the articulating surfaces to practically one plane; that is, the movements of the elbow are principally ones of flexion and extension. At the knee joint, on the other hand, the articulating surfaces offer no restraint to the movements of the joint. Rather restraining ligaments are required to restrict the movements of the knee joint to practically one plane. The movements of flexion and extension at the knee joint differ from those in a typical hinge joint, such as the elbow, in that the axis around which motion takes place shifts its position slightly during movement of the joint.

Figure 9:
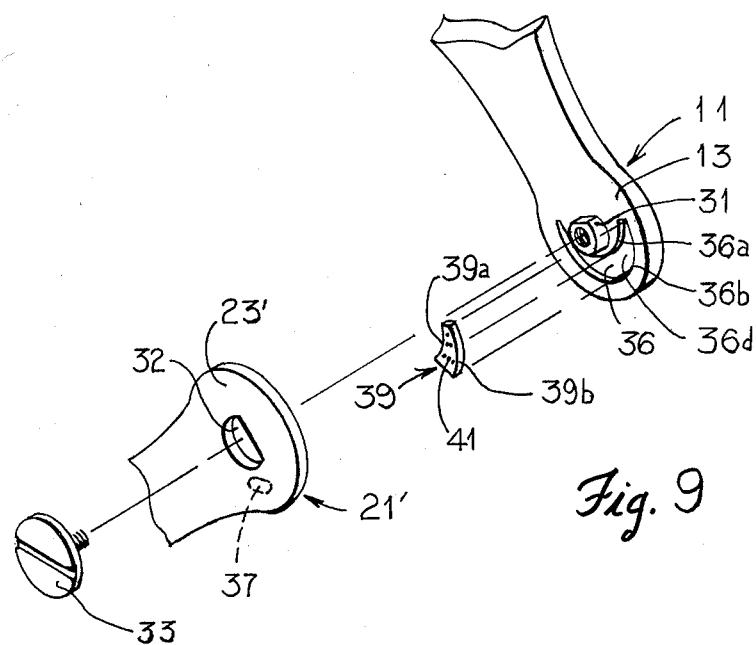
FIG. 9 is an exploded view on a reduced scale showing in perspective the parts of the joint structure according to the present invention for a lateral brace designed for use on the right knee or on the left elbow and for a medial brace designed for use on the left knee or on the right elbow and showing an accessory insert which may be used to limit the extension of the joint.

Referring now to the drawings, the present joint structure which is best seen in FIGS. 1 through 6 and in FIG. 9 essentially comprises a pair of pivotally interconnected joint elements 11 and 21. An eccentric member 31 with internal threads 38 protrudes from an inner face 14 of the end portion 13 into the guide 32 formed in the overlapping end portion 23. The eccentric member 31 is provided with a semi-cylindrical surface 31a and a shoulder 31b which is joined thereto, the shoulder and the semi-cylindrical surface being disposed at generally right angles to the inner face 14. As is best seen by comparing FIGS. 3 and 4, the radius of curvature of the semi-cylindrical surface 31a is substantially shorter than the radius of curvature of the curved edge surface 32a of the guide 32, thus allowing the axis around which motion takes place to shift, following the movements of a wearer's natural joint.

The eccentric member 31 and the retaining screw 33 which is threadedly engaged therewith comprise a means of retaining the joint elements 11 and 21 in overlapping relation. The overlapping end portion 23 slides between the plane surfaces of the juxtaposed end portion 13 and the enlarged head 34 of the retaining screw 33.

During flexion of the wearer's joint, the point at which the axis of rotation of the end portion 23 passes through the guide 32 shifts upward and forward with respect to the eccentric member 31 as illustrated in FIG. 5. Among joint structures incorporated in braces to protect knee joints, the present joint structure affords somewhat better protection of a joint from a lateral blow incurred when the knee joint is fully flexed than does a joint structure with a single pivot which does not protrude forward sufficiently to protect the sides of the flexed knee.

As is also illustrated in FIG. 5, the semicylindrical surface 31a of the eccentric member 31 functions as a bearing surface which is in sliding contact with a portion of the curved edge surface 32a of the guide 32 whenever, prior to the longitudinal alignment of the joint elements 11 and 21, the joint is under compressive loading during flexion of the wearer's joint. During the transition to full extension, as well as at full extension, any compressive loads on the joint are transmitted through an elongated pin 37 which is described hereinbelow. The joint mechanism provides ample support of a wearer's joint throughout the complete pivotal motion both vertically and laterally.

The end portion 23 has an elongated pin 37 which travels within a groove 36 formed in the contiguous, opposing face 14 of the overlapping end portion 13 (see FIGS. 1 and 5). The curved edge surfaces 36a and 36b of the groove 36 have radii of curvature of different lengths. The width of the groove 36 decreases toward the distal portion 36c thereof into which the pin 37 protrudes when the joint elements 11 and 21 are in longitudinal alignment (see FIG. 1). For the joint element 21' shown in FIG. 9, on the other hand, the width of the groove 36 decreases toward the distal portion 36d thereof since the pin 37 protrudes into the portion 36d when the joint elements 11 and 21' are in longitudinal alignment. It is not necessary that the distal portions 36d and 36c be of decreasing width in the joint elements 21 and 21', respectively, however.

In general, the movements of the joint elements 11 and 21 relative to each other are limited by the abutment, either simultaneously or at different times, of the eccentric member 31 and of the elongated pin 37 against the edge surfaces of the guide 32 and of the groove 36, respectively. That is, the elongated pin 37 limits the motion of the eccentric member 31 within the guide 32; and the motion of the pin 37 is in turn limited by the eccentric member 31. Specifically, in the preferred embodiment shown in FIGS. 1 through 6 and in FIG. 9, the eccentric member 31 moves only in that portion of the guide 32 which is disposed between the pin 37 and an arc which is generally centered about the pin 37 and which passes in close proximity to the centerline which bisects the guide 32 longitudinally.

The unique contours of the edge surfaces of the guide 32 and of the groove 36 provide a smooth transition from flexion to extension of the joint structure. As the degree of flexion is reduced, the pin 37 moves within the groove 36 until the pin 37 abuts the inner curved edge surface 36a (see FIG. 1). As the angle between the longitudinal axes of the joint elements 11 and 21 is further increased, the joint element 21 pivots about the interface between the narrow end 37a of the elongated pin 37 and the curved edge surface 36a until the shoulder 31b is brought into positive contact with the straight side edge 32b of the guide 32. The taper of the groove 36 near the distal portion 36c is sufficiently gradual in the joint element 21 that the eccentric member 31 readily crosses the guide 32 to abut the straight side edge 32b, thus allowing the joint to follow the natural movement of a wearer's joint.

As the joint element pivots about the pin 37, the pin simultaneously slides slightly further into the tapered distal portion 36c of the groove. The positive abutment of the shoulder 31b against the straight side edge 32b is thus coupled with a seating of the pin 37 within the tapered distal portion 36c to lock the joint with respect to increases in the angle between the longitudinal axes of the joint elements 11 and 21 beyond the angle of the limiting position. The joint elements 11 and 21 when the joint is so locked remain movable with respect to one another to one side of the limiting position. The preferred embodiment of the joint structure shown in FIGS. 1 through 6 has as its limiting position the one in which the joint elements 11 and 21 are in longitudinal alignment to prevent the hyperextension of a wearer's joint. An insert 39 shown in FIG. 9 may be used to alter the limiting position of the joint structure as described hereinbelow.

During the transition from a state of flexion of the wearer's joint to a state of full extension, any compressive load on the joint structure is born by the elongated pin 37 which is designed to withstand high stresses. As is illustrated in FIGS. 1 and 4, the pin 37 is preferably narrow in one direction to facilitate the seating of the pin in the tapered distal portion 36c but wide in a direction at right angles thereto to strengthen the pin so it can withstand the shear forces imposed thereon during the sequence described hereinabove in which the joint elements 11 and 21 become locked with respect to further extension. A bumper formed of rubber or the like may be inserted into the distal portion 36c to decelerate the motion of the pin 37 relative to the groove 36. This reduces the shear stresses both on the pin 37 and on the shoulder 31b which then abuts less forcefully against the straight edge surface 32b when the wearer's joint is abruptly extended.

As is illustrated in FIGS. 3 and 4, both the groove 36 and the guide 32 are disposed entirely away from the outer side edges 12 and 22 of the joint elements 11 and 21, respectively. Moreover, the groove 36 has a depth which is less than the thickness of the end portion 13 so that, in the assembled joint, the edge surfaces 36a and 36b are inaccessible from the outside. To make the guide similarly inaccessible, an enlarged head 34 for the retaining screw 33 is provided. The diameter of the head 34 is sufficiently large to cover the guide 32 for all of the configurations into which the joint elements 11 and 21 can move relative to each other (see FIGS. 1 and 5). Thus the guide 32 is totally enclosed in the assembled joint between the end portion 13 and the retaining screw 33, thereby eliminating the possibility that the joint can be jammed inadvertently with foreign objects. The joint according to the present invention thus has particular utility in severe environments, such as the playing fields of contact sports.

Figure 10:
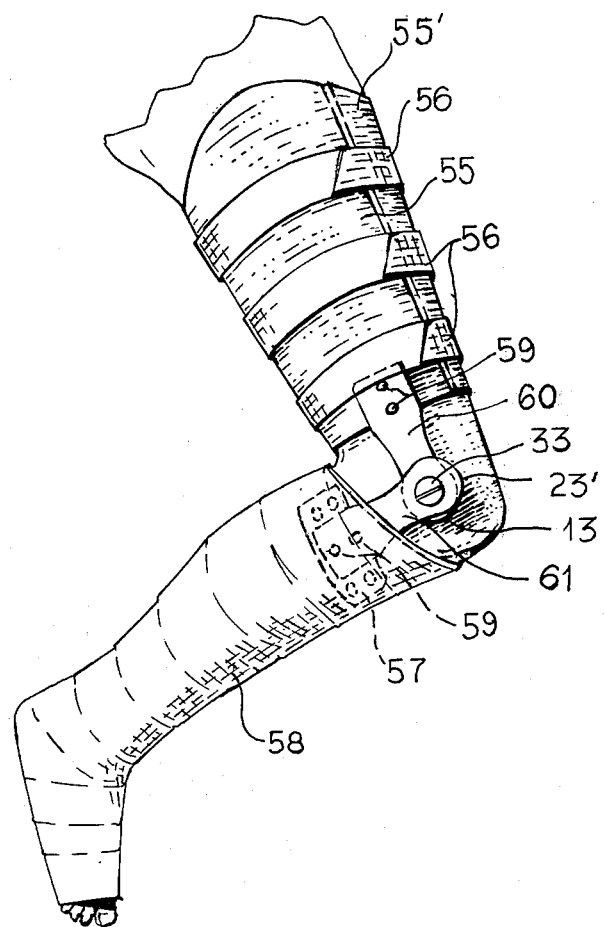
FIG. 10 is a side view of a partial cast including a side member of a knee brace incorporating the joint structure according to the present invention.

FIGS. 7, 8, and 10 illustrate practical applications of the present joint structure. As illustrated in FIGS. 7 and 8, a preferred brace incorporating the present joint structure for protecting the knee joint by inhibiting torsional twisting of a wearer's leg is one having a pair of lateral and medial side members 10, 20. The side members 10, 20 are substantially identical to one another except for the placement of the elongated pin 37 in the inner face of the joint element having the guide 32.

In the side member 20, the previously described joint elements 11 and 21 are formed as integral parts of the lower thigh support member 41 and the upper calf support member 52 which respectively encircle a portion of the thigh and calf of the user's leg (see FIG. 7). The support members 41, 52 are securely held in place by the improved straps 46. The straps 46 extend laterally from the buckles 43 on one side of the longitudinal axis of each of the support members 41, 52. The straps 46 which extend from the buckles 43 on one side of the support member 41 comprise a single, unitary piece formed of plastic. Likewise, the straps 46 extending from the buckles 43 on one side of the support member 52 comprise a single, unitary piece formed of plastic. Alternately, the straps 45 may be detachably secured to the buckles 43. The improved straps and buckles were previously described in my copending application Ser. No. 171,497.

Several features of the support members 41 and 52 distinguish them from the single pivot support members incorporated in the knee braces which were previously described in my copending applications Ser. Nos. 896,990 and 117,958. Not only does the present joint structure allow the brace in which the support members 41 and 52 are included to follow the wearer's natural joint movement more closely, thereby reducing any tendency of the brace to migrate up and down a wearer's leg, but also the improved straps 46 respond more quickly to the rolling and swelling of the athlete's leg during running. Moreover, the curved outer side edges of the buckles 43 enhance the capacity of the support members to conform to the changing contour of a wearer's leg. This results in less abrasion of a wearer's skin and in greater comfort generally for the user because he does not experience a feeling of constant binding or pressure from the straps.

An elastic cuff 47a composed preferably of a two-way stretch material may be worn beneath the support members 41, 51 to reduce further any chafing of the wearer's skin by the straps 46. A cloth strip may be stitched to the cuff 47 at regular intervals to form loops 48 (see FIG. 7). A buckle 43 extending laterally from one of the support members 41, 52 is inserted into each of the loops 48 once the elastic cuff is in place at the wearer's knee joint to reduce slippage between the support members 41, 52 and the elastic cuff 47a. Alternately, the straps 46 may be sheathed in cloth coverings 47b to protect the wearer's skin from abrasion (see FIG. 8).

As is seen in FIGS. 7 and 8, a padding 27 which is preferably thicker beneath the reinforcing abutment 25 formed in the support member 51, 52 and beneath the hump 26 formed in the support member 41 may be glued to the support members. The padding 27 is composed of an urethane foam which is sandwiched between a nylon mesh and a vinyl covering or the like. The placement of thicker padding beneath the abutment 25 and the hump 26 causes the joint structure to arch away from the wearer's knee joint (see FIG. 8). The force of lateral blow to this arch tends to be dissipated to the large muscles of a wearer's thigh and calf rather than absorbed by the knee joint.

The joint structure illustrated generally in FIGS. 1 through 6 and in FIG. 9 is also applicable to use in orthpedic or in surgical brace situations. A shallow, elongated cavity is formed at the interface between the overlapping end portion 23' and the groove 36. This cavity is inaccessible from the outside in the assembled joint. Prior to the assembly of the joint, however, one or more inserts 39 having curved side edges 39a and 39b may be placed within the groove 36. Each insert 39 comprises a means which is detachably mountable within the groove 36 for limiting the travel of the pin 37. With the inclusion of a pair of inserts within the groove 36 on either side of the elongated pin 37, the joint structure can be immobilized when required for the treatment of an injured or diseased joint.

When some flexion of the patient's joint is desirable, the limiting position of the longitudinal axes to one side of which the joint elements are movable with respect to one another may be adjusted so that the maximum angle allowable between the longitudinal axes of the joint elements is less than 180°. In the preferred embodiment illustrated in FIGS. 9 and 10, the maximum angle allowable between the longitudinal axes of the joint elements 11 and 21' has been reduced by the placement of a single insert 39 within the distal portion 36d. To facilitate the mounting of the insert 39, the radii of curvature of the side edges 39a and 39b thereof are approximately equal to the radii of curvature of the curved edge surfaces 36a and 36b, respectively. A cross-section of the groove 36 which intersects the insert 39 is substantially filled by it. With the insert 39 in place, the wearer's limb can be only partially extended.

As is illustrated in FIG. 9, the insert 39 has transverse lines of perforations 41a. The perforations 41a allow individual links to be easily separated from the insert 39. As the joint heals, the amount of relative motion allowable between the joint elements can be gradually increased by substituting an insert which has been shortened by the removal of one or more of the links. Thus a patient wearing a brace incorporating a joint structure according to the present invention to support an injured or diseased joint can exercise the affected limb in increasing amounts to reduce the degree of muscle atrophy and of joint stiffness which would otherwise develop if the joint were immobilized throughout the duration of the healing process.

The previously described joint elements 11 and 21' having end portions 13 and 23' are integrally formed as upwardly and downwardly extending uprights 60 and 61. The distal ends of the uprights 60 and 61 are rigidly attached by means of rivets 59 to a plastic sheet member 55 and to a flanged member 57, respectively. Alternatively, the distal ends of the uprights may be inserted into pockets formed in the plastic sheet member and in the flanged member. The plastic sheet member is preferably composed of a thermoplastic material such as that described in U.S. Pat. No. 3,906,943 which may be heated and shaped to conform to the contours of an individual user's limb. The plastic sheet member 55 together with a second plastic sheet member 55' which is attached to the upwardly extending upright of a support member on the opposite side of the patient's thigh completely encases the wearer's leg to form a solid plastic cast which is secured in place by means of conventional straps 56 or the like. A tape 58 having plaster of Paris embedded in it such as the Hexcelite Orthopaedic Tape manufactured by Zinco Industries, Inc., Montrose, CA, may be used to secure the flanged member 57 to the wearer's limb to form a partial cast. The use of connected lateral and media side members is preferred for maintaining lateral-medial stability in an application involving such a cast.

As described hereinabove, inserts 39 are detachably mounted in the groove 36 prior to the assembly of the joint structure in order to limit the movements of a patient's limb during its rehabilitation. Gradually, shorter inserts may be substituted to allow increased freedom of movement as healing occurs.

The eccentric member 31 and the end portion 13 are preferably fabricated together in one plastic injection operation as are the pin 37 and the end portion 23, 23'. In the preferred embodiments, the eccentric member 31 and the end portion 13 comprise a single, unitary piece formed of a self-lubricating plastic material such as polypropylene, polyethylene, nylon, or the like. Likewise, the elongated pin 37 and the end portion 23, 23' comprise a single, unitary piece formed of a self-lubricating plastic.

Preferably, the guide 32 is formed symmetrically on either side of the centerline which bisects the joint element longitudinally as shown in FIG. 4. If, during the injection molding operation, a second elongated pin is also formed symmetrically across the centerline on the inner face from the elongated pin 37, the same mold can be used to form both the end portions 23 and 23'. One of the elongated pins must be cut off leaving in its place a smooth surface coplanar with the inner face from which the remaining elongated pin protrudes. The placement of the elongated pin 37 as shown in FIG. 4, for example, is suitable for a joint element which is designed for use in a joint structure which is incorporated in a lateral side member worn on the outside of the left leg or in a medial side member 20 worn on the inner side of the right leg (see FIGS. 7 and 8). On the other hand, the placement of the elongated pin 37 as shown in FIG. 9, is suitable for a joint structure which is incorporated in a lateral side member worn on the outside of the right leg or in a medial side member worn on the inner side of the left leg.

What is claimed is:

1. A joint for use in knee braces and the like, comprising:
   first and second joint elements having overlapping end portions, the first joint element having a guide formed therein within the zone of overlap of the joint elements, the guide including a straight edge surface;
   a means connected to the second joint element for retaining the joint elements in overlapping relation, the retaining means having an eccentric member which protrudes into the guide, the eccentric member having a shoulder which abuts against the straight edge surface of the guide when the joint elements are aligned in a limiting position to one side of which the joint elements are movable with respect to one another;
   the second joint element having a groove formed therein within the zone of overlap of the joint elements, the groove having curved edge surfaces of differing radii of curvature, the width of the groove decreasing in a direction toward at least one distal portion thereof; and
   a pin connected to the first joint element which moves within the groove toward the end portion thereof having a decreasing width as the angle between the longitudinal axes of the joint elements is increased until the pin abuts one of the curved edge surfaces, the first joint element being pivotable about the interface between the pin and the curved edge surface to bring the shoulder into positive contact with the guide, thereby locking the joint with respect to any further increase in the angle between the longitudinal axes of the first and second joint elements.

2. A joint for use in knee braces and the like according to claim 1 wherein:
   the guide includes a curved edge surface connected to the straight edge surface; and
   the eccentric member includes a semi-cylindrical surface connected to the shoulder, the semi-cylindrical surface being in sliding contact with the curved edge surface of the guide whenever, prior to the alignment of the joint elements in the limiting position to one of side of which the joint elements are movable with respect to each other, a compressive load which is transmitted along one of the longitudinal axes of the joint elements is imposed upon the joint, thereby providing ample support of a wearer's joint during flexion.

3. A joint for use in knee braces and the like according to claim 1 wherein the depth of the groove is less than the thickness of the second joint element within the zone of overlap of the joint elements.

4. A joint for use in knee braces and the like according to claim 3 which further comprises a means which is detachably mountable within the groove for limiting the travel of the pin.

5. A joint for use in knee braces and the like according to claim 4 wherein the limiting means comprises at least one insert which is placed within the distal portion of the groove having a decreasing width so that a wearer's limb can be only partially extended.

6. A joint for use in knee braces and the like according to claim 3 wherein the retaining means further comprises a retaining screw which is threadedly engaged with the eccentric member, the head of the screw being of sufficiently large diameter to cover the guide for all of the configurations into which the first and second joint elements can move relative to one another, thereby eliminating the possibility of the joint being jammed inadvertently with foreign objects.

7. A joint for use in knee braces and the like according to claim 1 wherein the limiting position is one in which the joint elements are in longitudinal alignment.

8. A joint for use in knee braces and the like according to claim 1 wherein the limiting position is one in which the angle between the longitudinal axes of the joint elements is less than 180°.

9. A joint for use in knee braces and the like according to claim 1 wherein:
   the first joint element and the pin comprise a single, unitary piece formed of plastic; and
   the second joint element and the eccentric member comprise a single, unitary piece formed of plastic.

10. A joint for use in knee braces and the like according to claim 1 wherein the pin is elongate, thereby facilitating the seating of the pin in the distal portion of the groove having a decreasing width and strengthening the pin so that it can withstand the shear forces imposed upon it during the locking of the joint elements with respect to any further increase in the angle between the longitudinal axes of the first and second joint elements.

11. A joint for use in knee braces and the like, comprising:

first and second joint elements having overlapping end portions which are pivotally interconnected, the second joint element having a guide formed therein within the zone of overlap of the joint elements;

the first joint element having a groove formed therein within the zone of overlap of the joint elements, the groove having a distal portion of decreasing width;

a first means connected to the end portion of the first joint element which is disposed away from the side edges thereof for engaging the guide; and a second means connected to the second joint element which is disposed away from the side edges thereof for engaging the distal portion of the groove of decreasing width, the engagement of said distal portion by the second engaging means being coupled with the engagement of the guide by the first engaging means when the joint elements are aligned in a limiting position to one side of which the joint elements are movable with respect to one another.

* * * * *